US00PP18531P3

(12) United States Plant Patent
Olesen

(10) Patent No.: US PP18,531 P3
(45) Date of Patent: Feb. 26, 2008

(54) SHRUB ROSE PLANT NAMED 'POULTC010'

(50) Latin Name: *Rosa hybrida*
Varietal Denomination: Poultc010

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 121 days.

(21) Appl. No.: 11/389,461

(22) Filed: Mar. 23, 2006

(65) Prior Publication Data

US 2007/0226846 P1 Sep. 27, 2007

(51) Int. Cl.
*A01H 5/00* (2006.01)

(52) U.S. Cl. ..... Plt./102

(58) Field of Classification Search ..... Plt./102, Plt./107

See application file for complete search history.

*Primary Examiner*—Annette H Para

(57) ABSTRACT

A new garden rose plant of the shrub class which has abundant, pink flowers and attractive foliage. This new and distinct variety has shown to be uniform and stable in the resulting generations from asexual propagation.

1 Drawing Sheet

Botanical classfication: *Rosa hybrida.*
Variety denomination: 'Poultc010'.

SUMMARY OF THE INVENTION

The present invention constitutes a new and distinct variety of garden rose plant which originated from a controlled crossing between female parent plant an unnamed seedling and the male parent plant, an unnamed seedling. The two parents were crossed during the summer of 1997, and the resulting seeds were planted in a controlled environment in Fredensborg, Denmark. The new variety is named 'Poultc010'.

The new variety may be distinguished from the female parent by the following combination of characteristics:

1. 'Poultc010' has a very low growing and compact habit. The female parent plant is less compact in height.
2. 'Poultc010' exhibits flowers with a smaller diameter than those of the unnamed female parent.
3. 'Poultc010' develops more flowers on each branch than the parent.

The new variety may be distinguished from the pollen parent by the following combination of characteristics:

1. The pollen parent has a light pink flower color while 'Poultc010' has deep pink flowers.
2. The pollen parent has flowers which are 50 to 60 mm in diameter. Flowers of the claimed plant are normally 32 mm in diameter.

The objective of the hybridization of this rose variety was to create a new and distinct variety for garden use with unique qualities, such as:

1. Very compact plants with small leaves;
2. Abundant dark pink flowers;
3. Vigorous, but compact, growth when propagated both as a budded rose and on its own roots;
4. Exceptional disease resistance;
5. Suitability for container rose culture.

This combination of qualities is not present in previously available commercial cultivars of this type, known to the inventor, and distinguish 'Poultc010' from all other varieties of which we are aware.

As part of the rose development program Mogens N. Olesen germinated the seeds from the aforementioned hybridization during winter of 1997 and conducted evaluations on the resulting seedlings in a controlled environment in Fredensborg, Denmark.

'Poultc010' was selected in the spring 1998 by the inventor as a single plant from the progeny of the aforementioned hybridization.

Asexual reproduction of 'Poultc010' by traditional budding and rooted cuttings was first done by Mogens N. Olesen in Fredensborg, Denmark in July, 1998. This initial and other subsequent asexual propagations conducted in controlled environments have demonstrated that the characteristics of 'Poultc010' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poultc010'. Specifically illustrated in the drawing are.

DETAILED DESCRIPTION OF THE VARIETY

Figures 1A, 1B, 1C, 1D, 1E, 1F, 1G:
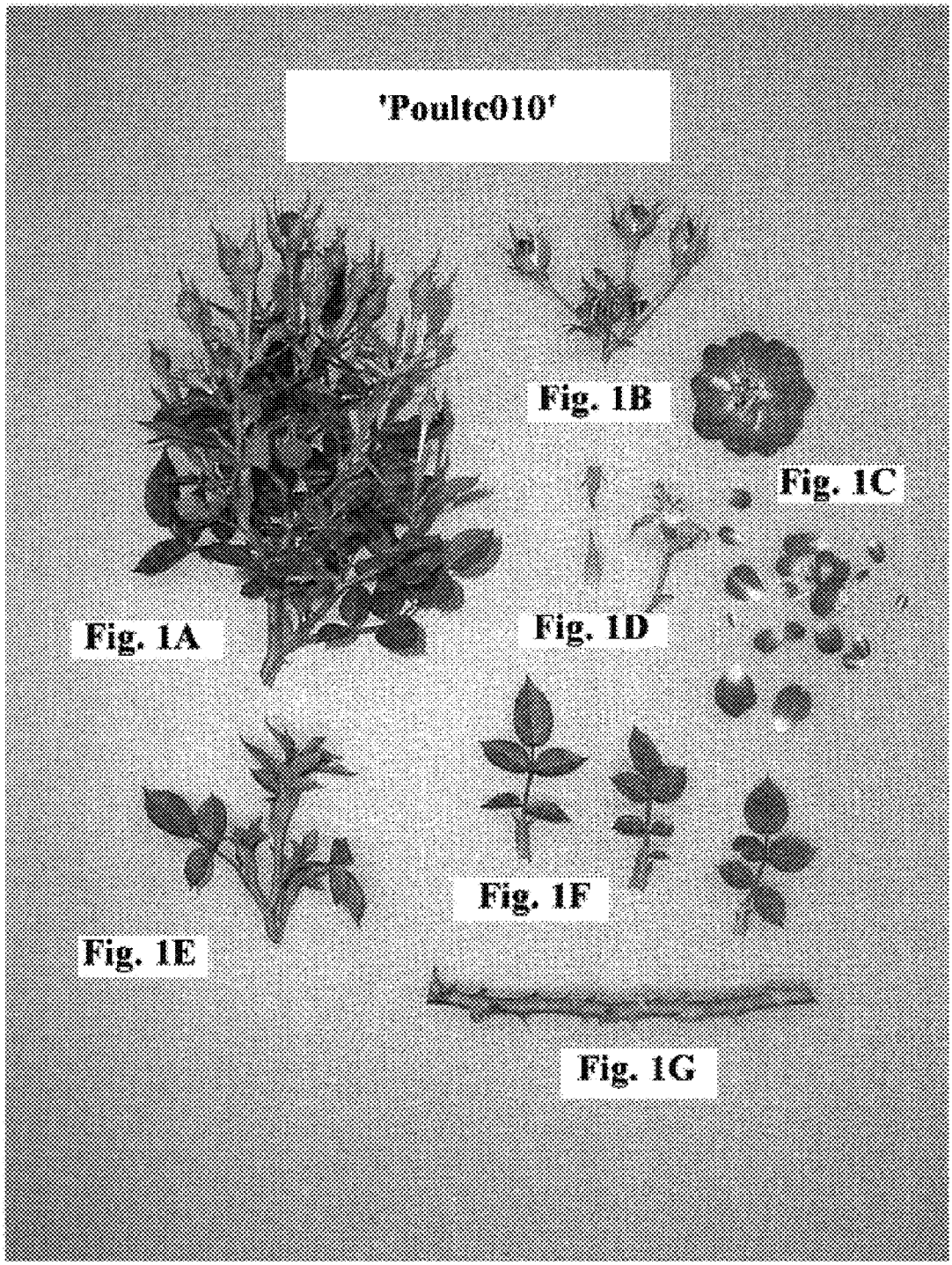
FIG. 1A; Full cluster of flower buds at the end of a flowering branch.
FIG. 1B; Small cluster of flower buds partially opened and open flower viewed from above.
FIG. 1C; Flower petals and petaloids, detached.
FIG. 1D; Sepals, receptacle, and peduncle.
FIG. 1E; Juvenile growth, attached to stem.
FIG. 1F; Mature leaves.
FIG. 1G; Bare stem exhibiting prickles.

The following is a description of 'Poultc010', as observed in its growth in a field nursery in Jackson County, Oreg. Observed plants are 3 years of age, grown on *Rosa multi-*

*flora* understock. Color references are made using The Royal Horticultural Society (London, England) Colour Chart, 1995, except where common terms of color are used.

For a comparison, several physical characteristics of the rose variety 'Poulor', a rose variety from the same inventor described and illustrated in U.S. Plant Pat. No. 12,511, are compared to 'Poultc010' in Chart 1.

CHART 1

| | 'Poultc010' | 'Poulor' |
|---|---|---|
| Sepal outer surface color | Yellow-Green Group 146B. | Green Group 143C. |
| Bud form | Pointed ovate. | Short, pointed ovoid. |
| General tonality | Red-Purple Group 58B to Red-Purple Group 57A. | Red-Purple Group 65A. |

FLOWER AND FLOWER BUD

Blooming habit: Continuous.

Flower bud:

*Size.*—Upon opening, 10 mm in length from base of receptacle to end of bud. Diameter is 6 mm.

*Bud form.*—Pointed ovate.

*Bud color.*—As sepals unfold, petals are Red-Purple Group 61B to Red-Purple Group 57A. Sepal Upper Surface: Color: Yellow-Green Group 146A and Yellow-Green Group 145C. Surface: Lightly pubescent. Sepal Lower Surface: Color: Yellow-Green Group 146B. Texture: Smooth. Sepal Shape: Sepal apex is cirrhose. Base is flat at union with receptacle. Sepal Margin: Margins have weak foliaceous appendages on three of the five sepals and few stipitate glands. Size: Normally 15 mm (l)×5 mm (w).

*Receptacle.*—Surface: Smooth. Shape: Urn shaped. Size: 4 mm (h)×4 mm (w). Color: Yellow-Green Group 144A.

*Pedicel.*—Surface: Somewhat rough with stipitate glands. Length: 7 to 10 mm average length. Diameter: 1 to 1.5 mm normally. Color: Yellow-Green Group 144A to 144B. Strength: Somewhat strong.

*Borne.*—In clusters resembling corymb with 7 to 9 flowers flowering branch.

Flower bloom:

*Fragrance.*—None.

*Duration.*—The blooms have a duration on the plant of approximately 7 to 10 days. Afterwards, petals fall cleanly away from plant.

*Size.*—Flower diameter is 32 mm on average when fully open. Depth is normally 10 mm.

*Form.*—Flowers open fully, almost flat.

*Shape of flower when viewed from the side.*—Upon opening, upper part: Flattened convex. Upon opening, lower part: Flat. Open flower, upper part: Flattened convex. Open flower, lower parts: Flat.

Petalage: 20 to 25 petals under normal conditions with an average of 3 petaloids.

Color:

*Upon opening, petals.*—Outermost petals: Outer side: Red-Purple Group 58B to 57A occasionally streaks of White Group 155D blended with Red-Purple Group 58D bisecting the petal. Inner Side: Red-Purple Group 58B to 57A occasionally streaks of White Group 155D blended with Red-Purple Group 58D bisecting the petal. Innermost petals: Outer side: Red-Purple Group 58B to 57A occasionally streaks of White Group 155D blended with Red-Purple Group 58D bisecting the petal. Inner Side: Red-Purple Group 58B to 57A occasionally streaks of White Group 155D blended with Red-Purple Group 58D bisecting the petal.

*Upon opening, basal petal spots.*—Outer side: White Group 155B. Inner Side: White Group 155B.

*After opening, petals.*—Outermost petals: Outer side: Red-Purple Group 58C with intonations of Red-Purple Group 57A. Inner Side: Red-Purple Group 58C with intonations of Red-Purple Group 57A. Innermost petals: Outer side: Red-Purple Group 58C with intonations of Red-Purple Group 57A. Inner Side: Red-Purple Group 58C with intonations of Red-Purple Group 57A.

*After opening, basal petal spots.*—Outer side: White Group 155B. Inner Side: White Group 155B.

General tonality: On open flowers are Red-Purple Group 58B to Red-Purple Group 57A. No change in tonality at the end of the $7^{th}$ day. Afterwards, general tonality fades slightly to become Red-Purple Group 58C.

Petals:

*Petal reflex.*—Outer petals slightly reflexed.

*Margin.*—Entire with point at center of the margin, occasionally cleft appearing at apex.

*Shape.*—Narrow elliptical. Apex: Orbicular to cuspidate. Base: Acute.

*Size.*—Variable. Inner petals are 14 mm (l)×9 mm (w). Outer petals 17 mm (l)×14 mm (w).

*Texture.*—Smooth.

*Thickness.*—Thin.

*Arrangement.*—Not Formal.

Petaloids:

*Quantity.*—Normally 3.

*Color.*—Upper Surface: White Group 155B to Red-Purple Group 58C. Lower Surface: White Group 155B to Red-Purple Group 58C.

*Size.*—On average, 7 mm (l)×3 mm (w).

*Shape.*—Narrow elliptic. Base is very acute.

Reproductive organs:

*Pistils.*—Length: 3 to 4 mm. Quantity: 15 to 20 normally.

*Pollen.*—None observed.

*Anthers.*—Size: Generally 1 mm in length. Color: Greyed-Orange Group 163C. Quantity: 45 average.

*Filaments.*—Color: Yellow-Green Group 145D. Length: 3 to 4 mm.

*Stigmas.*—Level in location to the length of the filaments and the height of the anthers. Color: Yellow-Green Group 144D.

*Styles.*—Color: Yellow-Green Group 149B/C.

*Hips.*—None Observed.

PLANT

Plant growth: Bushy, low growing and very compact. When grown as a budded field grown plant on *Rosa multiflora* understock, the average height of the plant is 40 to 60 cm. The average spread of the plant is 45 cm.

Stems:

*Color.*—Young wood: Yellow-Green Group 146B. Older wood: Yellow-Green Group 146B.

*Length.*—6 to 8 mm.

*Diameter.*—3.5 mm average.

*Internodes.*—Normally 10 mm.

*Surface texture.*—Young wood: Smooth. Older wood: Smooth.

Prickles:

*Incidence.*—8 prickles s per 10 cm of stem.

*Color.*—Juvenile prickles: Greyed-Red Group 181C. Mature prickles: Greyed-Yellow Group 160D.

*Shape.*—Upper side: Convex. Lower side: Concave.

Plant foliage: 7 leaflets on normal leaves in middle of the stem.

*Compound leaf size.*—55 to 60 mm (l)×25 to 30 mm (w).

*Quantity.*—8 to 10 leaves per 10 cm of stem on average.

*Color.*—Mature Foliage: Upper surface: Green Group 137A. Lower surface: Yellow-Green Group 147B. Juvenile Foliage: Upper surface: Green Group 143C with marginal anthocyanin intonations Greyed-Red Group 181A. Lower surface: Yellow-Green Group 144B.

Plant leaves and leaflets:

*Stipules.*—Size: Normally 10 mm. Margins: Finely serrated with stipitate glands. Color: Yellow-Green Group 144A.

*Petiole.*—Length: Normally 10 mm. Diameter: 1 mm on average. Upper surface: Color: Yellow-Green Group 145C and Yellow-Green Group 146A. Lower surface: Color: Yellow-Green Group 144A. Observations: Few stipitate glands at upper surface. Few small prickles on lower surface.

*Rachis.*—Length: Normally 28 mm. Above: Color: Yellow-Green Group 146A. Underneath: Color: Yellow-Green Group 144A. Observations: Few stipitate glands at upper surface. Few small prickles on lower surface.

*Leaflet.*—Size: Normally 20 mm (l)×13 mm (w). Edge: Serrated. Shape: Generally ovate. Base: Obtuse. Apex: Acuminate. Texture: Smooth. Thickness: Thin. Arrangement: Odd pinnate. Venation: Reticulate. Glossiness: Somewhat glossy.

Disease resistance: Above average resistance to powdery and downy mildew, rust, black spot, and *Botrytis* under normal growing conditions in Jackson County, Oreg.

Cold hardiness: The variety 'Poultc010' has been found to be cold tolerant to USDA Cold Hardiness Zone 6.

It is claimed:

1. A new and distinct variety of rose plant of the shrub rose class named 'Poultc010', substantially as illustrated and described herein due to its abundant pink flowers, compact growth habit, disease resistance, and extended period of bloom.

* * * * *

'Poultc010'